United States Patent
Phan et al.

(10) Patent No.: US 9,888,926 B2
(45) Date of Patent: Feb. 13, 2018

(54) APPARATUS AND METHOD FOR DEPLOYING STENT ACROSS ADJACENT TISSUE LAYERS

(75) Inventors: Hoang Phan, Freemont, CA (US); John Lunsford, San Carlos, CA (US); Kenneth F. Binmoeller, Rancho Santa Fe, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 296 days.

(21) Appl. No.: 13/364,265

(22) Filed: Feb. 1, 2012

(65) Prior Publication Data
US 2012/0136426 A1    May 31, 2012

Related U.S. Application Data

(63) Continuation of application No. 12/772,762, filed on May 3, 2010, now Pat. No. 8,357,193.
(Continued)

(51) Int. Cl.
*A61B 17/11* (2006.01)
*A61B 17/00* (2006.01)
(Continued)

(52) U.S. Cl.
CPC .... *A61B 17/1114* (2013.01); *A61B 17/00234* (2013.01); *A61B 17/11* (2013.01); *A61F 2/95* (2013.01); *A61F 2/966* (2013.01); *A61B 17/0218* (2013.01); *A61B 17/2909* (2013.01); *A61B 2017/00278* (2013.01); *A61B 2017/00336* (2013.01); *A61B 2017/00862* (2013.01); *A61B 2017/1107* (2013.01); *A61B 2017/1139* (2013.01); *A61B 2017/22038* (2013.01); *A61B 2017/3484* (2013.01); *A61B 2217/005* (2013.01); *A61M 27/002* (2013.01)

(58) Field of Classification Search
USPC .................................. 623/1.12, 23.64–23.67
See application file for complete search history.

(56) References Cited

U.S. PATENT DOCUMENTS

| | | | |
|---|---|---|---|
| 2,127,903 | A | 8/1938 | Bowen |
| 3,039,468 | A | 6/1962 | Price |

(Continued)

FOREIGN PATENT DOCUMENTS

| | | |
|---|---|---|
| CN | 2845770 Y | 12/2006 |
| CN | 2925418 Y | 7/2007 |

(Continued)

OTHER PUBLICATIONS

Chopita et al.; Endoscopic gastroenteric anastomosis using magnets; Endoscopy; 37(4); pp. 313-317; Apr. 2005.
(Continued)

*Primary Examiner* — Leslie Lopez

(57) ABSTRACT

Transluminal access system includes a stent delivery catheter having a handle control mechanism. The catheter comprises a number of components for establishing an initial penetration between adjacent body lumens and subsequently implanting a stent or other luminal anchor therebetween. Manipulation of the stent components is achieved using control mechanisms on the handle while the handle is attached to an endoscope which provides access to a first body lumen.

24 Claims, 8 Drawing Sheets

Related U.S. Application Data

(60) Provisional application No. 61/182,312, filed on May 29, 2009.

(51) Int. Cl.
*A61F 2/95* (2013.01)
*A61F 2/966* (2013.01)
*A61B 17/02* (2006.01)
*A61B 17/22* (2006.01)
*A61B 17/34* (2006.01)
*A61B 17/29* (2006.01)
*A61M 27/00* (2006.01)

(56) References Cited

U.S. PATENT DOCUMENTS

| | | |
|---|---|---|
| 3,717,151 A | 2/1973 | Collett |
| 3,874,388 A | 4/1975 | King et al. |
| 3,970,090 A | 7/1976 | Loiacono |
| 4,173,392 A | 11/1979 | Ekinaka et al. |
| 4,235,238 A | 11/1980 | Ogiu et al. |
| 4,587,972 A | 5/1986 | Morantte, Jr. |
| 4,608,965 A | 9/1986 | Anspach, Jr. et al. |
| 4,705,040 A | 11/1987 | Mueller et al. |
| 4,790,813 A | 12/1988 | Kensey |
| 4,869,263 A | 9/1989 | Segal et al. |
| 4,896,678 A | 1/1990 | Ogawa |
| 4,917,097 A | 4/1990 | Proudian et al. |
| 4,920,967 A | 5/1990 | Cottonaro et al. |
| 4,950,285 A | 8/1990 | Wilk |
| 4,973,317 A | 11/1990 | Bobrove |
| 4,990,139 A | 2/1991 | Jang |
| 5,024,655 A | 6/1991 | Freeman et al. |
| 5,064,435 A | 11/1991 | Porter |
| 5,180,392 A | 1/1993 | Skeie et al. |
| 5,183,464 A | 2/1993 | Dubrul |
| 5,197,971 A | 3/1993 | Bonutti |
| 5,207,229 A | 5/1993 | Winters |
| 5,209,727 A | 5/1993 | Radisch, Jr. et al. |
| 5,211,651 A | 5/1993 | Reger et al. |
| 5,221,258 A | 6/1993 | Shturman |
| 5,224,945 A | 7/1993 | Pannek, Jr. |
| 5,226,421 A | 7/1993 | Frisbie et al. |
| 5,234,447 A | 8/1993 | Kaster et al. |
| 5,246,007 A | 9/1993 | Frisbie et al. |
| 5,246,445 A | 9/1993 | Yachia et al. |
| 5,257,990 A | 11/1993 | Nash |
| 5,258,000 A | 11/1993 | Gianturco |
| 5,261,920 A | 11/1993 | Main et al. |
| 5,275,610 A | 1/1994 | Eberbach |
| 5,275,611 A | 1/1994 | Behl |
| 5,290,249 A | 3/1994 | Foster et al. |
| 5,304,198 A | 4/1994 | Samson |
| 5,330,497 A | 7/1994 | Freitas et al. |
| 5,353,785 A | 10/1994 | Wilk |
| 5,368,595 A | 11/1994 | Lewis |
| 5,372,588 A | 12/1994 | Farley et al. |
| 5,381,788 A | 1/1995 | Matula et al. |
| 5,395,349 A | 3/1995 | Quiachon et al. |
| 5,425,739 A | 6/1995 | Jessen |
| 5,443,484 A | 8/1995 | Kirsch et al. |
| 5,458,131 A | 10/1995 | Wilk |
| 5,462,561 A | 10/1995 | Voda |
| 5,470,337 A | 11/1995 | Moss |
| 5,495,851 A | 3/1996 | Dill et al. |
| 5,520,700 A | 5/1996 | Beyar et al. |
| 5,531,699 A * | 7/1996 | Tomba et al. ............ 604/170.02 |
| 5,536,248 A | 7/1996 | Weaver et al. |
| 5,588,432 A | 12/1996 | Crowley |
| 5,601,588 A | 2/1997 | Tonomura et al. |
| 5,603,698 A | 2/1997 | Roberts et al. |
| 5,620,456 A | 4/1997 | Sauer et al. |
| 5,620,457 A | 4/1997 | Pinchasik et al. |
| 5,662,664 A | 9/1997 | Gordon et al. |
| 5,681,345 A | 10/1997 | Euteneuer |
| 5,688,247 A | 11/1997 | Haindl et al. |
| 5,697,944 A | 12/1997 | Lary |
| 5,709,671 A | 1/1998 | Stephens et al. |
| 5,709,707 A | 1/1998 | Lock et al. |
| 5,709,713 A | 1/1998 | Evans et al. |
| 5,713,870 A | 2/1998 | Yoon |
| 5,725,552 A | 3/1998 | Kotula et al. |
| 5,797,906 A | 8/1998 | Rhum et al. |
| 5,817,062 A | 10/1998 | Flom et al. |
| 5,827,276 A | 10/1998 | LeVeen et al. |
| 5,843,116 A | 12/1998 | Crocker et al. |
| 5,843,127 A | 12/1998 | Li |
| 5,853,421 A | 12/1998 | Leschinsky et al. |
| 5,853,422 A | 12/1998 | Huebsch et al. |
| 5,855,576 A | 1/1999 | LeVeen et al. |
| 5,857,999 A | 1/1999 | Quick et al. |
| 5,858,006 A | 1/1999 | Van der Aa et al. |
| 5,882,340 A | 3/1999 | Yoon |
| 5,893,856 A | 4/1999 | Jacob et al. |
| 5,897,567 A | 4/1999 | Ressemann et al. |
| 5,935,107 A | 8/1999 | Taylor et al. |
| 5,944,738 A | 8/1999 | Amplatz et al. |
| 5,951,576 A | 9/1999 | Wakabayashi |
| 5,951,588 A | 9/1999 | Moenning |
| 5,957,363 A | 9/1999 | Heck |
| 5,993,447 A | 11/1999 | Blewett et al. |
| 6,007,522 A | 12/1999 | Agro et al. |
| 6,007,544 A | 12/1999 | Kim |
| 6,017,352 A | 1/2000 | Nash et al. |
| 6,022,359 A | 2/2000 | Frantzen |
| 6,036,698 A | 3/2000 | Fawzi et al. |
| 6,063,113 A | 5/2000 | Kavteladze et al. |
| 6,074,416 A | 6/2000 | Berg et al. |
| 6,080,174 A | 6/2000 | Dubrul et al. |
| 6,113,609 A | 9/2000 | Adams |
| 6,113,611 A | 9/2000 | Allen et al. |
| 6,152,144 A | 11/2000 | Lesh et al. |
| 6,190,353 B1 | 2/2001 | Makower et al. |
| 6,228,039 B1 | 5/2001 | Binmoeller |
| 6,231,515 B1 | 5/2001 | Moore et al. |
| 6,231,587 B1 | 5/2001 | Makower |
| 6,241,758 B1 | 6/2001 | Cox |
| 6,251,084 B1 | 6/2001 | Coelho |
| 6,264,675 B1 | 7/2001 | Brotz |
| 6,290,485 B1 | 9/2001 | Wang |
| 6,309,415 B1 | 10/2001 | Pulnev et al. |
| 6,315,708 B1 | 11/2001 | Salmon et al. |
| 6,322,495 B1 | 11/2001 | Snow et al. |
| 6,334,446 B1 | 1/2002 | Beyar |
| 6,348,064 B1 | 2/2002 | Kanner |
| 6,358,264 B2 | 3/2002 | Banko |
| 6,371,964 B1 | 4/2002 | Vargas et al. |
| 6,371,965 B2 | 4/2002 | Gifford et al. |
| 6,391,036 B1 | 5/2002 | Berg et al. |
| 6,402,770 B1 | 6/2002 | Jessen |
| 6,432,040 B1 | 8/2002 | Meah |
| 6,436,119 B1 | 8/2002 | Erb et al. |
| 6,447,524 B1 | 9/2002 | Knodel et al. |
| 6,454,765 B1 | 9/2002 | LeVeen et al. |
| 6,468,303 B1 | 10/2002 | Amplatz et al. |
| 6,475,168 B1 | 11/2002 | Pugsley, Jr. et al. |
| 6,475,185 B1 | 11/2002 | Rauker et al. |
| 6,475,222 B1 | 11/2002 | Berg et al. |
| 6,485,496 B1 | 11/2002 | Suyker et al. |
| 6,488,653 B1 | 12/2002 | Lombardo |
| 6,508,252 B1 | 1/2003 | Berg et al. |
| 6,520,908 B1 | 2/2003 | Ikeda et al. |
| 6,535,764 B2 | 3/2003 | Imran et al. |
| 6,547,776 B1 | 4/2003 | Gaiser et al. |
| 6,575,967 B1 | 6/2003 | LeVeen et al. |
| 6,610,100 B2 | 8/2003 | Phelps et al. |
| 6,614,595 B2 | 9/2003 | Igarashi |
| 6,616,675 B1 | 9/2003 | Evard et al. |
| 6,620,122 B2 | 9/2003 | Stinson et al. |
| 6,626,917 B1 | 9/2003 | Craig |
| 6,626,919 B1 | 9/2003 | Swanstrom |
| 6,632,197 B2 | 10/2003 | Lyon |
| 6,635,068 B1 | 10/2003 | Dubrul et al. |
| 6,638,213 B2 | 10/2003 | Ogura et al. |

(56) References Cited

U.S. PATENT DOCUMENTS

| | | |
|---|---|---|
| 6,645,205 B2 | 11/2003 | Ginn |
| 6,656,182 B1 | 12/2003 | Hayhurst |
| 6,656,206 B2 | 12/2003 | Corcoran et al. |
| 6,669,708 B1 | 12/2003 | Nissenbaum et al. |
| 6,682,536 B2 | 1/2004 | Vardi et al. |
| 6,736,828 B1 | 5/2004 | Adams et al. |
| 6,746,472 B2 | 6/2004 | Frazier et al. |
| 6,746,489 B2 | 6/2004 | Dua et al. |
| 6,749,621 B2 | 6/2004 | Pantages et al. |
| 6,773,440 B2 | 8/2004 | Gannoe et al. |
| 6,835,189 B2 | 12/2004 | Musbach et al. |
| 6,846,323 B2 | 1/2005 | Yip et al. |
| 6,902,535 B2 | 6/2005 | Eberhart et al. |
| 6,916,332 B2 | 7/2005 | Adams |
| 6,921,361 B2 | 7/2005 | Suzuki et al. |
| 6,921,387 B2 | 7/2005 | Camrud |
| 6,942,678 B2 | 9/2005 | Bonnette et al. |
| 6,960,233 B1 | 11/2005 | Berg et al. |
| 6,966,917 B1 | 11/2005 | Suyker et al. |
| 6,974,467 B1 | 12/2005 | Gonzales, Jr. |
| 6,979,290 B2 | 12/2005 | Mourlas et al. |
| 7,018,401 B1 | 3/2006 | Hyodoh et al. |
| 7,056,325 B1 | 6/2006 | Makower et al. |
| 7,077,850 B2 | 7/2006 | Kortenbach |
| 7,131,948 B2 | 11/2006 | Yock |
| 7,150,723 B2 | 12/2006 | Meguro et al. |
| 7,153,314 B2 | 12/2006 | Laufer et al. |
| 7,156,857 B2 | 1/2007 | Pasricha et al. |
| 7,169,161 B2 | 1/2007 | Bonnette et al. |
| 7,182,771 B1 | 2/2007 | Houser et al. |
| 7,204,842 B2 | 4/2007 | Geitz |
| 7,273,451 B2 | 9/2007 | Sekine et al. |
| 7,303,531 B2 | 12/2007 | Lee et al. |
| 7,309,341 B2 | 12/2007 | Ortiz et al. |
| 7,361,180 B2 | 4/2008 | Saadat et al. |
| 7,377,897 B1 | 5/2008 | Kunkel et al. |
| 7,390,323 B2 | 6/2008 | Jang |
| 7,416,554 B2 | 8/2008 | Lam et al. |
| 7,429,264 B2 | 9/2008 | Melkent et al. |
| 7,534,247 B2 | 5/2009 | Ortiz |
| 7,591,828 B2 | 9/2009 | Ortiz |
| 7,637,919 B2 | 12/2009 | Ishikawa et al. |
| 7,731,693 B2 | 6/2010 | Melsheimer |
| 7,758,565 B2 | 7/2010 | Melsheimer |
| 7,785,275 B2 | 8/2010 | Melsheimer |
| 7,845,536 B2 | 12/2010 | Viola et al. |
| 7,914,552 B2 | 3/2011 | Shelton |
| 7,942,890 B2 | 5/2011 | D'Agostino et al. |
| 7,998,155 B2 | 8/2011 | Manzo |
| 8,034,063 B2 | 10/2011 | Binmoeller |
| 8,187,289 B2 | 5/2012 | Tacchino et al. |
| 8,197,498 B2 | 6/2012 | Coleman et al. |
| 8,926,545 B2 | 1/2015 | Brenneman et al. |
| 9,179,899 B2 | 11/2015 | Freudenthal |
| 2001/0004699 A1 | 6/2001 | Gittings et al. |
| 2001/0011170 A1 | 8/2001 | Davison et al. |
| 2002/0004663 A1 | 1/2002 | Gittings et al. |
| 2002/0161341 A1* | 10/2002 | Stinson et al. ............... 604/264 |
| 2002/0183787 A1 | 12/2002 | Wahr et al. |
| 2002/0188301 A1 | 12/2002 | Dallara et al. |
| 2003/0014063 A1 | 1/2003 | Houser et al. |
| 2003/0032975 A1 | 2/2003 | Bonutti |
| 2003/0040803 A1 | 2/2003 | Rioux et al. |
| 2003/0045893 A1 | 3/2003 | Ginn |
| 2003/0050665 A1 | 3/2003 | Ginn |
| 2003/0069533 A1 | 4/2003 | Kakutani et al. |
| 2003/0073979 A1 | 4/2003 | Naimark et al. |
| 2003/0078604 A1 | 4/2003 | Walshe |
| 2003/0088256 A1 | 5/2003 | Conston et al. |
| 2003/0093118 A1 | 5/2003 | Ho et al. |
| 2003/0109900 A1 | 6/2003 | Martinek |
| 2003/0120292 A1 | 6/2003 | Park et al. |
| 2003/0163017 A1 | 8/2003 | Tam et al. |
| 2003/0199991 A1 | 10/2003 | Stack et al. |
| 2003/0216749 A1 | 11/2003 | Ishikawa et al. |
| 2003/0236536 A1 | 12/2003 | Grigoryants et al. |
| 2004/0019322 A1 | 1/2004 | von Hoffmann |
| 2004/0034371 A1 | 2/2004 | Lehman et al. |
| 2004/0044364 A1 | 3/2004 | DeVries et al. |
| 2004/0049157 A1 | 3/2004 | Plishka et al. |
| 2004/0073108 A1 | 4/2004 | Saeed et al. |
| 2004/0122456 A1 | 6/2004 | Saadat et al. |
| 2004/0199087 A1 | 10/2004 | Swain et al. |
| 2004/0215220 A1 | 10/2004 | Dolan et al. |
| 2004/0236346 A1 | 11/2004 | Parker |
| 2004/0243122 A1 | 12/2004 | Auth et al. |
| 2004/0249335 A1 | 12/2004 | Faul et al. |
| 2004/0249985 A1 | 12/2004 | Mori et al. |
| 2004/0260332 A1 | 12/2004 | Dubrul et al. |
| 2005/0022843 A1 | 2/2005 | Policicchio et al. |
| 2005/0033327 A1 | 2/2005 | Gainor et al. |
| 2005/0043759 A1 | 2/2005 | Chanduszko |
| 2005/0043781 A1 | 2/2005 | Foley |
| 2005/0059890 A1 | 3/2005 | Deal et al. |
| 2005/0059990 A1 | 3/2005 | Ayala et al. |
| 2005/0075654 A1 | 4/2005 | Kelleher |
| 2005/0096685 A1 | 5/2005 | Murphy et al. |
| 2005/0113868 A1 | 5/2005 | Devellian et al. |
| 2005/0187567 A1 | 8/2005 | Baker et al. |
| 2005/0228413 A1 | 10/2005 | Binmoeller et al. |
| 2005/0251159 A1 | 11/2005 | Ewers et al. |
| 2005/0251208 A1 | 11/2005 | Elmer et al. |
| 2005/0277981 A1 | 12/2005 | Maahs et al. |
| 2006/0015006 A1 | 1/2006 | Laurence et al. |
| 2006/0062996 A1 | 3/2006 | Chien et al. |
| 2006/0111672 A1 | 5/2006 | Seward |
| 2006/0116697 A1 | 6/2006 | Carter et al. |
| 2006/0142703 A1 | 6/2006 | Carter et al. |
| 2006/0142790 A1 | 6/2006 | Gertner |
| 2006/0167482 A1 | 7/2006 | Swain et al. |
| 2006/0190021 A1 | 8/2006 | Hausman et al. |
| 2006/0190075 A1 | 8/2006 | Jordan et al. |
| 2006/0200177 A1 | 9/2006 | Manzo |
| 2006/0217748 A1 | 9/2006 | Ortiz |
| 2006/0217762 A1* | 9/2006 | Maahs et al. ............... 606/213 |
| 2006/0224183 A1 | 10/2006 | Freudenthal |
| 2006/0253088 A1 | 11/2006 | Chow et al. |
| 2006/0259051 A1 | 11/2006 | Nissl |
| 2006/0259074 A1 | 11/2006 | Kelleher et al. |
| 2006/0282087 A1 | 12/2006 | Binmoeller |
| 2007/0027534 A1 | 2/2007 | Bergheim et al. |
| 2007/0066863 A1 | 3/2007 | Rafiee et al. |
| 2007/0112363 A1 | 5/2007 | Adams |
| 2007/0112380 A1 | 5/2007 | Figulla et al. |
| 2007/0112383 A1 | 5/2007 | Conlon et al. |
| 2007/0123840 A1 | 5/2007 | Cox |
| 2007/0123917 A1 | 5/2007 | Ortiz et al. |
| 2007/0123934 A1 | 5/2007 | Whisenant et al. |
| 2007/0135825 A1* | 6/2007 | Binmoeller ............... 606/153 |
| 2007/0179426 A1 | 8/2007 | Selden |
| 2007/0197862 A1 | 8/2007 | Deviere et al. |
| 2007/0213812 A1 | 9/2007 | Webler et al. |
| 2007/0260273 A1 | 11/2007 | Cropper et al. |
| 2007/0265656 A1 | 11/2007 | Amplatz et al. |
| 2008/0009888 A1 | 1/2008 | Ewers et al. |
| 2008/0045989 A1 | 2/2008 | Welborn |
| 2008/0065012 A1 | 3/2008 | Hebert et al. |
| 2008/0071301 A1 | 3/2008 | Matsuura et al. |
| 2008/0077180 A1 | 3/2008 | Kladakis et al. |
| 2008/0132999 A1 | 6/2008 | Mericle et al. |
| 2008/0140172 A1 | 6/2008 | Carpenter et al. |
| 2008/0161645 A1 | 7/2008 | Goldwasser et al. |
| 2008/0167524 A1 | 7/2008 | Goldwasser et al. |
| 2008/0183080 A1 | 7/2008 | Abraham |
| 2008/0215089 A1 | 9/2008 | Williams et al. |
| 2008/0243151 A1 | 10/2008 | Binmoeller et al. |
| 2008/0249481 A1 | 10/2008 | Crainich et al. |
| 2008/0249562 A1 | 10/2008 | Cahill |
| 2009/0024149 A1 | 1/2009 | Saeed et al. |
| 2009/0030380 A1 | 1/2009 | Binmoeller |
| 2009/0062841 A1 | 3/2009 | Amplatz et al. |
| 2009/0082803 A1 | 3/2009 | Adams et al. |
| 2009/0105733 A1 | 4/2009 | Coleman et al. |
| 2009/0138071 A1 | 5/2009 | Cheng et al. |

(56) References Cited

U.S. PATENT DOCUMENTS

| | | | |
|---|---|---|---|
| 2009/0143713 A1* | 6/2009 | Van Dam et al. | 604/9 |
| 2009/0143759 A1 | 6/2009 | Van Dam et al. | |
| 2009/0143760 A1 | 6/2009 | Van Dam et al. | |
| 2009/0177288 A1 | 7/2009 | Wallsten | |
| 2009/0187214 A1 | 7/2009 | Amplatz et al. | |
| 2009/0210048 A1 | 8/2009 | Amplatz et al. | |
| 2009/0227835 A1 | 9/2009 | Terliuc | |
| 2009/0259288 A1 | 10/2009 | Wijay et al. | |
| 2009/0281379 A1 | 11/2009 | Binmoeller et al. | |
| 2009/0281557 A1 | 11/2009 | Sander et al. | |
| 2010/0048990 A1 | 2/2010 | Bakos | |
| 2010/0105983 A1 | 4/2010 | Oneda et al. | |
| 2010/0130993 A1 | 5/2010 | Paz et al. | |
| 2010/0168557 A1 | 7/2010 | Deno et al. | |
| 2010/0191167 A1 | 7/2010 | Laufer | |
| 2010/0241218 A1 | 9/2010 | Bruszewski et al. | |
| 2010/0256775 A1 | 10/2010 | Belhe et al. | |
| 2010/0261962 A1 | 10/2010 | Friedberg | |
| 2010/0268029 A1 | 10/2010 | Phan et al. | |
| 2010/0268175 A1 | 10/2010 | Lunsford et al. | |
| 2011/0054381 A1 | 3/2011 | Van Dam et al. | |
| 2011/0060398 A1 | 3/2011 | Tupil et al. | |
| 2011/0087146 A1 | 4/2011 | Ryan et al. | |
| 2011/0098531 A1 | 4/2011 | To | |
| 2011/0112622 A1 | 5/2011 | Phan et al. | |
| 2011/0137394 A1 | 6/2011 | Lunsford et al. | |
| 2013/0006347 A1 | 1/2013 | McHugo | |
| 2013/0012969 A1 | 1/2013 | Shin | |
| 2013/0253546 A1 | 9/2013 | Sander et al. | |
| 2016/0095599 A1 | 4/2016 | Jose et al. | |

FOREIGN PATENT DOCUMENTS

| | | |
|---|---|---|
| DE | 102006050385 | 4/2008 |
| EP | 637431 A1 | 2/1995 |
| EP | 1314404 A2 | 5/2003 |
| EP | 1520526 A1 | 4/2005 |
| EP | 1520532 A2 | 4/2005 |
| EP | 1857135 A2 | 11/2007 |
| EP | 1894514 A2 | 3/2008 |
| GB | 2020557 A | 11/1979 |
| JP | S58-35219 | 3/1983 |
| JP | 62-233168 | 10/1987 |
| JP | H05-137794 A | 6/1993 |
| JP | H05-192407 A | 8/1993 |
| JP | H05-329165 | 12/1993 |
| JP | H05-508563 | 12/1993 |
| JP | H07-096038 | 4/1995 |
| JP | 08-071158 A | 3/1996 |
| JP | 8-504940 | 5/1996 |
| JP | 8-509639 | 10/1996 |
| JP | H08-299455 A | 11/1996 |
| JP | H09-500047 A | 1/1997 |
| JP | H09-504186 A | 4/1997 |
| JP | 09-140804 A | 6/1997 |
| JP | 10-94543 | 4/1998 |
| JP | 10-155799 A | 6/1998 |
| JP | H11-512318 A | 10/1999 |
| JP | 2000-500045 A | 1/2000 |
| JP | 2000-237303 | 9/2000 |
| JP | 2000-237303 A | 9/2000 |
| JP | 2001-511658 | 8/2001 |
| JP | 2001-275947 | 10/2001 |
| JP | 2001-517524 A | 10/2001 |
| JP | 2002-119516 | 4/2002 |
| JP | 2002-524196 | 8/2002 |
| JP | 2002-534208 A | 10/2002 |
| JP | 2002-542872 | 12/2002 |
| JP | 2003-509175 | 3/2003 |
| JP | 2003-526448 | 9/2003 |
| JP | 2004-512153 | 4/2004 |
| JP | 2004-216192 | 8/2004 |
| JP | 2005-525865 | 9/2005 |
| JP | 2007514462 | 6/2007 |
| JP | 2008-534029 A | 8/2008 |
| JP | 2009500051 | 1/2009 |
| WO | WO 97/27898 A1 | 8/1997 |
| WO | WO 99/23952 A1 | 5/1999 |
| WO | WO 00/24449 A1 | 5/2000 |
| WO | WO 00/72909 A1 | 12/2000 |
| WO | WO 01/21247 A1 | 3/2001 |
| WO | WO 01/72367 A1 | 10/2001 |
| WO | WO 03/020106 A2 | 3/2003 |
| WO | WO 03/024305 A2 | 3/2003 |
| WO | WO 03/071962 A2 | 9/2003 |
| WO | WO 2005/011463 A2 | 2/2005 |
| WO | WO 2005/096953 A1 | 10/2005 |
| WO | WO 2006/115811 A1 | 11/2006 |
| WO | WO 2007/047151 A1 | 4/2007 |
| WO | WO 2007115117 A1 | 10/2007 |
| WO | 2008/005510 | 1/2008 |
| WO | WO 2008/005888 A2 | 1/2008 |
| WO | 2010/011445 | 1/2010 |
| WO | WO 2010/011445 A1 | 1/2010 |

OTHER PUBLICATIONS

Fritscher-Ravens et al.; A through-the-scope device for suturing and tissue approximation under EUS control; Gastro Endo; 56(5); pp. 737-742; Nov. 2002.

Fritscher-Ravens et al.; Transgastric gastropexy and hiatal hernia repair for GERD under EUS control: A porcine model; Gastro Endo; 59(1); pp. 89-95; Jan. 2004.

Kahaleh et al.; Interventional EUS-guided cholangiography: evaluation of a technique in evolution; Gastrointestinal Endoscopy; 64(1); pp. 52-59; Jul. 2006.

Kwan et al.; EUS-guided cholecystenterostomy: a new technique; Gastrointestinal Endoscopy; 66(3); pp. 582-586; Sep. 2007.

Swain et al.; Knot tying at flexible endoscopy; gastro endo; 40(6); pp. 722-729; Nov. 1994.

Lepulu et al.; U.S. Appl. No. 13/281,410 entitled "Apparatus and Method for Penetrating and Enlarging Adjacent Tissue Layers," filed Oct. 25, 2011.

Lepulu et al.; U.S. Appl. No. 13/363,297 entitled "Apparatus and Method for Penetrating and Enlarging Adjacent Tissue Layers," filed Jan. 31, 2012.

Maisin et al.; Patency of endoscopic cystoduodenostomy maintained by a Z stent; Gastrointestinal Endoscopy; 40(6); pp. 765-768; Nov. 1994.

Binmoeller, Kenneth F.; U.S. Appl. No. 13/709,960 entitled "Method and Apparatus for Performing Needle Guided Interventions," filed Dec. 10, 2012.

Binmoeller et al.; U.S. Appl. No. 13/865,098 entitled "Luminal Structure Anchoring Devices and Methods," filed Apr. 17, 2013.

Brown et al.; U.S. Appl. No. 13/871,978 entitled "Methods and devices for access across adjacent tissue layers," filed Apr. 26, 2013.

Blum et al.; Endoluminal stent-grafts for infrarenal abdominal aortic aneurysms; NEJM; 336(1); pp. 13-20; Jan. 2, 1996.

Spillner et al.; Initial clainical experiences with endovascular stent-grafts for treatment of infrarenal abdominal aortic aneurysm (in German w/ English Summary); Zentralbl Chir.; 121(9); pp. 727-733; 1996 (year of pub. sufficiently earlier than effective US filing date and any foreign priority date).

Binmoeller et al.; U.S. Appl. No. 14/186,994 entitled "Devices and methods for forming an anastomosis," filed Feb. 21, 2014.

Rieder, E. et al., "Endoscopic suture fixation of gastrointestinal stents: proof of biomechanical principles and early clinical experience," Endoscopy, 2012, vol. 44, No. 12, pp. 1121-1126.

* cited by examiner

APPARATUS AND METHOD FOR DEPLOYING STENT ACROSS ADJACENT TISSUE LAYERS

CROSS REFERENCE TO RELATED APPLICATIONS

This application is a continuation of U.S. application Ser. No. 12/772,762, filed on May 3, 2010 which claims benefit of provisional application No. 61/182,312, filed on May 29, 2009, the full disclosures of which are incorporated herein by reference. The disclosure of the present application is related to those of commonly owned copending application Ser. No. 12/427,215, filed on Apr. 21, 2009; Ser. No. 12/757,408, filed on Apr. 9, 2010, and Ser. No. 12/757,421, filed on Apr. 9, 2010, the full disclosures of which are incorporated herein by reference.

FIELD

1. Field of the Invention

The present invention relates generally to medical devices and methods. More particularly, the present invention relates to inter-luminal stents and anchors as well as catheters and methods for their deployment.

A number of inter-luminal endoscopic procedures require precise placement of tissue anchors or stents. For example, a number of procedures may be performed by entering the gastrointestinal (GI) tract through a first organ or structure, such as the esophagus, stomach, duodenum, small intestine, or large intestine, and delivering the anchor or stent to adjacent organs and structures such as the bile duct, the pancreatic duct, the gallbladder, the pancreas, cysts, pseudocysts, abscesses, and the like.

Such endoscopic procedures often require the delivery of a tissue anchor or stent to secure adjacent tissues or organs and optionally to provide an opening therebetween. Inter-luminal tissue anchors, typically referred to as stents when they include a central lumen, are used to enable fluid communication between adjacent ducts, organs or lumens. Often, precise placement of the tissue anchor or stent is necessary, especially when the tissue anchor or stent has well defined anchoring elements at the proximal and/or distal ends, the device is used to secure adjacent lumens, or the device is placed within a duct at a precise location and secured at the proximal and/or distal ends.

When deploying a stent or other tissue anchor between adjacent body lumens, organs, or other structures, it is typically necessary to penetrate a wall of both the first body lumen through which access is established and a wall of a second body lumen which is the target of the procedure. When initially forming such access penetrations, there is significant risk of leakage from either the access body lumen or organ. In some cases, such as when accessing the bile duct, loss of the body fluid into surrounding tissues and body cavities can present substantial risk to the patient. Thus, it would be desirable to be able to establish the initial penetrations needed to deploy a stent or anchor while minimizing the risk of body fluid leakage. The risk of body fluid leakage can be exacerbated when multiple catheters or other tools are needed for placement of the stent or other anchor. In particular, the need to exchange tools over a guidewire or through an access catheter can both prolong the procedure and increase the risk of body fluid leakage during the procedure.

Thus, it would be desirable to minimize both the time and the number of tools which are needed when endoscopically placing stents or other anchors between adjacent body lumens or organs.

It would be further desirable to provide catheters and access tools which are capable of being deployed from endoscopes to access adjacent body lumens or cavities while minimizing the risk of leakage. It would be particularly desirable to provide catheters and tools which include all elements and capabilities needed to both penetrate the luminal walls and place the stent or other anchor between said walls, thus eliminating the need to exchange tools during an access procedure. It would be still further desirable if such tools and access methods could continually apply tension on the luminal walls to maintain said walls in close apposition during the stent or other anchor placement, thus further reducing the risk of body fluid loss during the procedure prior to final deployment of the stent or other tissue anchor. At least some of these objectives will be met by the inventions described below.

BACKGROUND

2. Description of the Background Art

US2009/0281379 and US2009/0281557 describe stents and other tissue anchors of the type that can be deployed by the apparatus and methods of the present invention. The full disclosures of these publications are incorporated herein by reference. US 2003/069533 describes an endoscopic trans-duodenal biliary drainage system which is introduced through a penetration, made by a trans-orally advanced catheter having a needle which is advanced from the duodenum into the gallbladder. U.S. Pat. No. 6,620,122 describes a system for placing a self-expanding stent from the stomach into a pseudocyst using a needle and an endoscope. US 2005/0228413, commonly assigned with the present application, describes a tissue-penetrating device for endoscopy or endosonography-guided (ultrasonic) procedures where an anchor may be placed to form an anastomosis between body lumens, including the intestine, stomach, and gallbladder. See also U.S. Pat. No. 5,458,131; U.S. Pat. No. 5,495,851; U.S. Pat. No. 5,944,738; U.S. Pat. No. 6,007,522; U.S. Pat. No. 6,231,587; U.S. Pat. No. 6,655,386; U.S. Pat. No. 7,273,451; U.S. Pat. No. 7,309,341; US 2004/0243122; US 2004/0249985; US 2007/0123917; WO 2006/062996; EP 1314404 Kahaleh et al. (2006) Gastrointestinal Endoscopy 64:52-59; and Kwan et al. (2007) Gastrointestinal Endoscopy 66:582-586. Shaped balloons having differently sized segments and segments with staged opening pressures are described in U.S. Pat. Nos. 6,835,189; 6,488,653; 6,290,485; 6,022,359; 5,843,116; 5,620,457; 4,990,139; and 3,970,090.

SUMMARY OF THE DISCLOSURE

The present invention provides methods and apparatus for establishing transluminal access between a first body lumen and a second body lumen. Such transluminal access may be intended for any medical purpose but will usually be intended for performing transluminal therapeutic endoscopy where the first body lumen is typically within the gastrointestinal (GI) tract, including the esophagus, the stomach, the duodenum, the small intestines, and the large intestines. The second body lumen, which is the target of the access, will typically be an organ or other tissue structure which lies adjacent to the gastrointestinal tract (or may be another part of the GI tract), including the bile duct, the pancreatic duct, the gallbladder, cysts, pseudocysts, abscesses, the pancreas, the liver, the urinary bladder, the duodenum, jejunum, and colon. Particular procedures which may benefit from the access methods and apparatus of the present invention include gastrojejunostomy, gastroduodenostomy, and gastrocolostomy. Other procedures which can benefit from the methods and apparatus of the present invention include vascular bypass including porto systemic shunts and transjugular intrahepatic portasystemic shunt (TIPS) procedures.

The methods and systems of the present invention are advantageous in a number of ways. For example, by providing an ability to dock a stent or anchor deployment catheter with an endoscope introduced to the first body lumen, a very stable platform is provided for sequentially accessing tools to penetrate the luminal walls, maintain the luminal walls in apposition, and deploy the stent or other anchor while the luminal walls are maintained in apposition. By maintaining a substantially continuous apposition of the walls at all times after the initial penetration, the risk of body fluid leakage into body cavities surrounding the lumens is minimized. A further advantage provided by the methods and systems herein is the elimination of the need to deploy a guidewire. By deploying a penetrating needle from the stent/anchor placement catheter to form the initial penetration and subsequently introducing the stent delivery tool(s) over the needle using the same catheter, the duration of the procedure can be reduced and the need to exchange tools over the guidewire is eliminated. A still further advantage provided by the methods and apparatus of the present invention is the ability to deploy a tension wire from the needle which is initially used to penetrate the luminal walls. By deploying an anchor on the distal end of the tension wire on the luminal wall of the second body lumen, tension can be maintained to hold the luminal walls in apposition while the stent/anchor delivery tool is advanced over the needle.

The stents and anchors which are deployed by the methods and apparatus of the present invention will have distal and proximal flange elements which, at the end of the implantation procedure, will engage the luminal walls and hold the luminal walls together. In addition, the flanges and stent/anchor will seal sufficiently against the luminal walls to inhibit leakage from the time of their initial deployment. Usually, the stent/anchors will include or define a central opening or passage to allow the exchange of fluid between the first body lumen and the second body lumen, often being drainage of fluid from the second body lumen into the first body lumen, e.g., for gallbladder or bile duct drainage. A number of suitable stent/anchors are described in co-pending application US 2009/0281557, the full disclosure of which is incorporated herein by reference.

In a first aspect of the present invention a device is used to deliver a tissue stent or anchor in a controlled and predetermined manner. The controlled delivery device is introduced through the working channel of an endoscope and includes a proximal handle that provides control of delivery and a catheter that extends from a distal end of the proximal handle to the distal end of the device. The handle has a coupling member for removable attachment to the endoscope to provide a stable deployable platform. The catheter includes an outer sheath, at least one shaft (e.g., an inner catheter or pusher tube) that is used to deploy the tissue anchor, and a tapered distal tip. The handle has coaxial sliding elements that control at least three operations, including device catheter positioning, distal anchor deployment, and proximal tissue anchor deployment. Such devices and apparatus will typically further include a first lock and a second lock for securing the first sliding element and the second sliding element, respectively. The ability to lock the sliding elements allows deployment of other components of the apparatus while maintaining the same relative position of the locked components.

The shaft and sheath of the catheter of the apparatus will be coaxially disposed so that the stent or anchor may be held over the shaft and constrained by the sheath. Thus, when using a self-expanding stent or anchor, the distal stent or anchor can be deployed by retracting the sheath over the stent or anchor while maintaining constraint of the proximal stent/anchor until deployment is desired. As described in more detail below, this allows the distal flange to be deployed and used to pull back on the wall of the second body lumen to maintain apposition as the proximal flange is deployed to complete the stent/anchor implantation.

Usually, the catheter shaft will have an axial passage extending therethrough. In some embodiments, the axial passage may be adapted to receive a guidewire. Usually, however, the catheter will further comprise a needle which is slidably disposed in the axial passage of the shaft. The needle will have a tissue penetrating tip, usually being sharpened, pointed or having an electrosurgical element, and will be operatively connected to a third slider or actuator on the handle, allowing a user to deploy the needle from the catheter, while the catheter is attached to the endoscope, in order to initially penetrate the luminal walls. Immediately after penetrating the luminal walls, the shaft and sheath of the catheter may be advanced over the needle to pass through the penetration in the luminal walls. Usually, the distal tip of the shaft will be tapered or have a cutting element to facilitate opening the passage through the luminal walls. The sheath may then be refracted over the shaft, again using the slider on the handle, in order to deploy the stent/anchor as discussed above.

In a still further specific aspect, the device may include a tension wire which is slidably disposed in an axial passage of the needle. The tension wire has an anchor at its distal end which can engage a wall of the second body lumen to provide tension as the catheter shaft and sheath are advanced over the needle. Typically, the anchor comprises a self-expanding structure formed integrally with the tension wire, usually comprising a plurality of loops which deploy rearwardly to form a concave structure or the wall of the second body lumen, e.g. where the concave structure provides clearance for advancing the catheter shaft and sheath past the luminal walls. A particular advantage of the concave structure is that it will protect against accidental needle penetrations after the anchor is deployed.

In a second aspect of the invention, methods for delivering a stent or other luminal anchor from a first body lumen to a second body lumen comprise advancing an endoscope having a working channel through the first body lumen to a target site on a wall of the first lumen. A stent deployment catheter is advanced through the working channel of the endoscope, and a handle control mechanism on the stent deployment catheter is attached to the endoscope so that the handle is immobilized relative to said endoscope. The stent deployment catheter assembly includes a shaft, a self-expanding stent (or anchor structure) carried on the shaft, and a sheath constraining the stent on the shaft, and the handle is used to sequentially manipulate the various catheter components in order to deploy the stent. Usually, the catheter assembly is advanced from the first body lumen, through the apposed walls at the target site and into the second body lumen through a passage in the luminal walls. After positioning the catheter, the sheath is retracted relative to the endoscope handle and shaft by a distance sufficient to release a distal portion of the stent to form a distal flange. The stent deployment assembly may then be pulled proximally, typically using controls on the handle, to engage the distal flange against the wall of the second body lumen to draw the two luminal walls into closer apposition. The sheath is then further retracted relative to the endoscope, handle and shaft to release the remaining portion of the stent to deploy a proximal flange against the wall of the first body lumen.

In some embodiments, the passage through which the stent deployment catheter is advanced may be pre-formed with separate tool(s), for example using trocars or other instruments as described in co-pending application Ser. No. 12/757,408, the full disclosure of which is incorporated herein by reference. More usually, however, the passage through the luminal walls will be formed by advancing a needle carried by the stent deployment catheter relative to the handle and endoscope to penetrate the needle through the apposed luminal walls. When using the "on-board" needle, the stent deployment catheter may then be advanced over the needle and through the apposed walls after the needle has penetrated the apposed walls. Preferably, tension will be applied to the apposed walls while the stent deployment catheter is advanced, typically by positioning an anchor on a tension wire on the luminal wall of the second body lumen. In the exemplary embodiments, the tension wire is deployed through an axial passage in the needle. Applying tension reduces the chance of accidental leakage of body fluids during the stent deployment. Alternatively, tension could be applied using separately deployed T-tags or other tethers.

In this specific embodiment, the stent deployment catheter is advanced by manually advancing a catheter slider on the handle, where the catheter slider is coupled to the catheter assembly to move the shaft, sheath, and stent in unison relative to the handle and endoscope. Similarly, retracting the sheath will comprise manually retracting a second slider on the handle, typically a collar on the catheter slider, where the second slider is coupled to the sheath to move the sheath relative to the shaft, the stent, handle, and endoscope. Thirdly, advancing the needle will typically comprise manually advancing a needle slider on the handle, where the needle slider is coupled to said needle to move the needle (which optionally carries the tension wire) relative to the shaft, stent, handle, and endoscope. In contrast, the tension wire and anchor are typically deployed by direct manual movement of a proximal end of the wire which extends through the central passage of the needle and out of the proximal end of the handle.

In a third aspect of the present invention, a catheter for delivering a self-expanding stent through apposed luminal walls comprises a shaft, a needle, a tension wire, a self-expanding stent, and a retractable sheath. The shaft has a distal end, a proximal end, and an axial passage therethrough. The needle is slidably positioned in the axial passage of the shaft and has a tissue-penetrating distal tip that can be advanced distally beyond the distal end of the shaft and retracted proximally within the passage of the shaft. The needle also has an axial passage therethrough, and the tension wire is slidably positioned in the axial passage of the needle. The tension wire includes a deployable anchor at its distal end where the anchor can be distally advanced beyond the distal tip of the needle and proximally retracted into the axial passage of the needle. The self-expanding stent is carried coaxially over the shaft and is constrained by the retractable sheath which is disposed thereover, as well as over the shaft. By proximally retracting the sheath, the stent can be released from constraint to deploy across the luminal walls.

The catheter typically further comprises a handle having a body with a coupling member that can be removably secured to a proximal end of an endoscope to position the catheter shaft within a working channel of the endoscope. The handle usually includes a catheter slide actuator to selectively advance and retract the catheter shaft within the working channel of the endoscope while the handle is secured to the endoscope. The handle usually also includes a second slide actuator, typically a collar on the catheter slide actuator, to selectively advance and retract the sheath over the shaft to release the self-expanding sheath from constraint. Additionally, a needle slide actuator is usually provided to selectively advance and retract the needle relative to the shaft.

The anchor on the tension wire may have a variety of configurations, but will usually be a self-expanding structure formed integrally with the tension wire. In this specific example, the self-expanding structure comprises a plurality of loops which deploy rearwardly to form a concave structure over the wall of the second body lumen, where the concave structure provides clearance for advancing the shaft and sheath through the luminal walls and protects the needle tip to inhibit accidental punctures.

The catheter may further comprise a port disposed on or otherwise coupled to a proximal end of the needle. The port may be used for aspiration and/or perfusion through the axial passage of the needle. For example, the port can allow for detection of when the needle has been advanced into the second body lumen as fluid from the second lumen may be aspirated through the port.

In the fourth aspect, the present invention provides methods for delivering a stent or other luminal anchor from the first body lumen, through apposed luminal walls, to a second body lumen. The method comprises positioning an endoscope in the first body lumen adjacent to a target site on a luminal wall. A catheter assembly is advanced through a working channel of the endoscope to locate a distal region of the catheter assembly at the target site. A needle carried by the catheter assembly may then be penetrated through the apposed walls at the target site, and an anchor on the distal end of a tension wire deployed in the second body lumen, typically from an axial passage within the needle. By drawing proximally on the tension wire (usually together with the needle), tension may be maintained on the walls to maintain the walls in close apposition to inhibit leakage of body fluids. A stent deployment sub-assembly which carries the stent is then advanced over the needle while maintaining tension on the tension wire. A distal flange on the stent may be expanded in the second body lumen, and the stent deployment sub-assembly drawn proximally to pull the distal flange against the wall of the second body lumen to maintain the walls in apposition, allowing the anchor on the tension wire to be withdrawn. While maintaining the walls in apposition with the distal flange, the proximal flange on the stent may be expanded in the lumen to complete the implantation. The catheter may then be withdrawn from the body lumens.

In particular instances, the anchor may be deployed by advancing the tension wire through an axial passage of the needle after the needle has penetrated through the apposed walls. The anchor will usually be self-expanding and be formed integrally with the tension wire. Thus, the self-expanding anchor will deploy as the tension wire is advanced from the needle allowing the anchor to be released from the constraint of the axial passage of the needle. In specific examples, the self-expanding structure comprises a plurality of loops which deploy rearwardly to form a concave structure over the wall of the second body lumen, where the concave structure provides clearance for advancing the stent deployment sub-assembly across the walls.

In most embodiments, the stent will also be self-expanding and be deployed by retracting a sheath which is part of the stent deployment sub-assembly. Usually, the sheath will be sequentially retracted to first deploy the distal flange and, after drawing the distal flange against the wall of the second body lumen, the sheath may be further retracted to deploy the proximal flange and complete implantation of the stent across the luminal walls.

DETAILED DESCRIPTION

Figure 1:
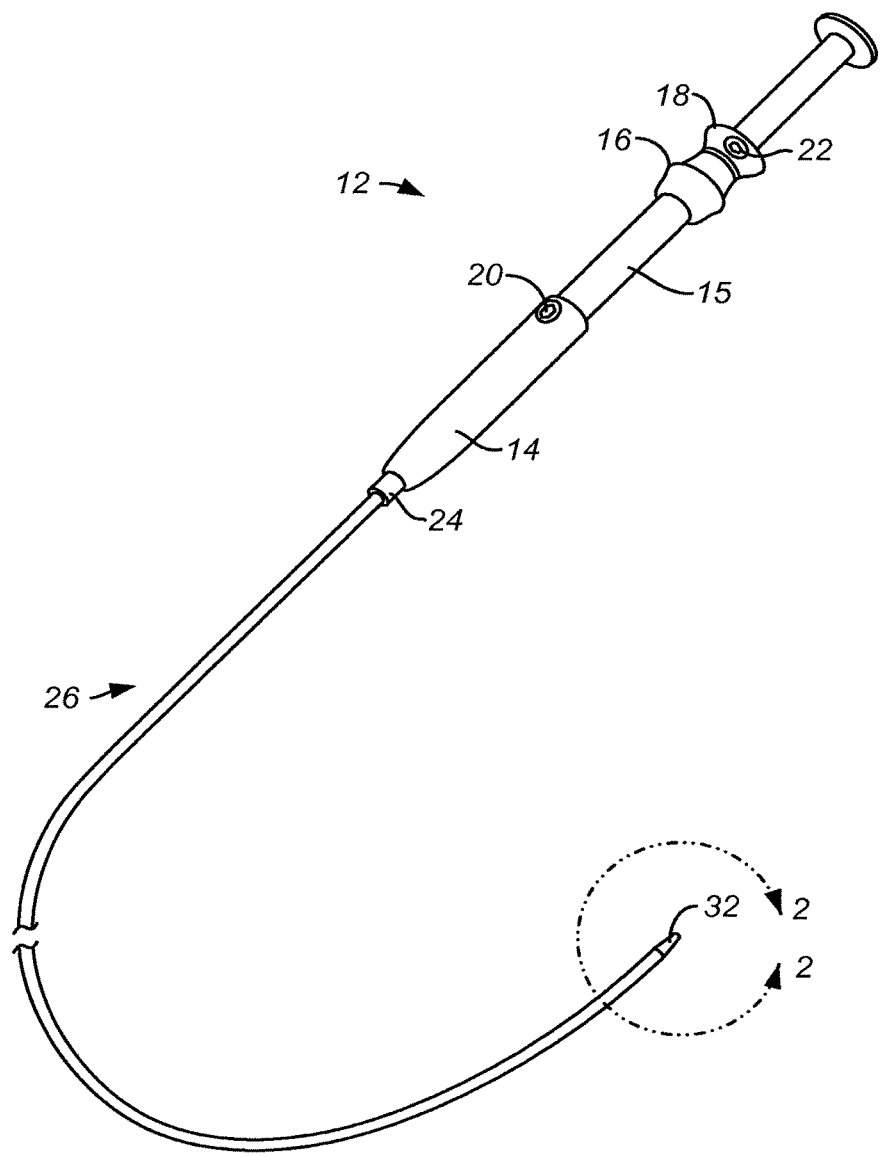
FIG. 1 illustrates a first embodiment of a stent deployment apparatus constructed in accordance with the principles of the present invention.
Figure 2:
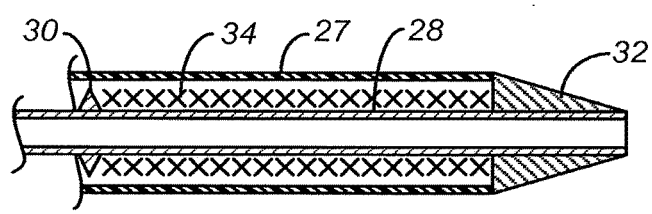
FIG. 2 is a cross-sectional view of the distal end of the stent deployment apparatus of FIG. 1, taken along line 2-2 of FIG. 1.

The device 10 of FIG. 1 includes a control handle 12 having a body 14 with a first slide actuator 15 with knob 16 and lock 20. A second slide actuator 18 with lock 22, scope locking mechanism 24, catheter body 26, a sheath 27, shaft 28, stent lock 30, distal tapered tip 32 and stent or other tissue anchor 34 (FIG. 2).

The distal end of endoscope or echo-endoscope 40 (FIG. 3A-3E) is positioned usually via trans-oral entry adjacent to a target location within the GI tract. A puncture is made at the desired location using a 19 gauge needle (typically an electrosurgical needle) followed by placement of a guidewire 102 through the needle lumen and optional balloon dilation over the guidewire or by using an expanding trocar as described in co-pending application Ser. No. 12/757,408 filed on Apr. 9, 2010, the full disclosure of which was previously incorporated herein by reference.

Figure 3A:
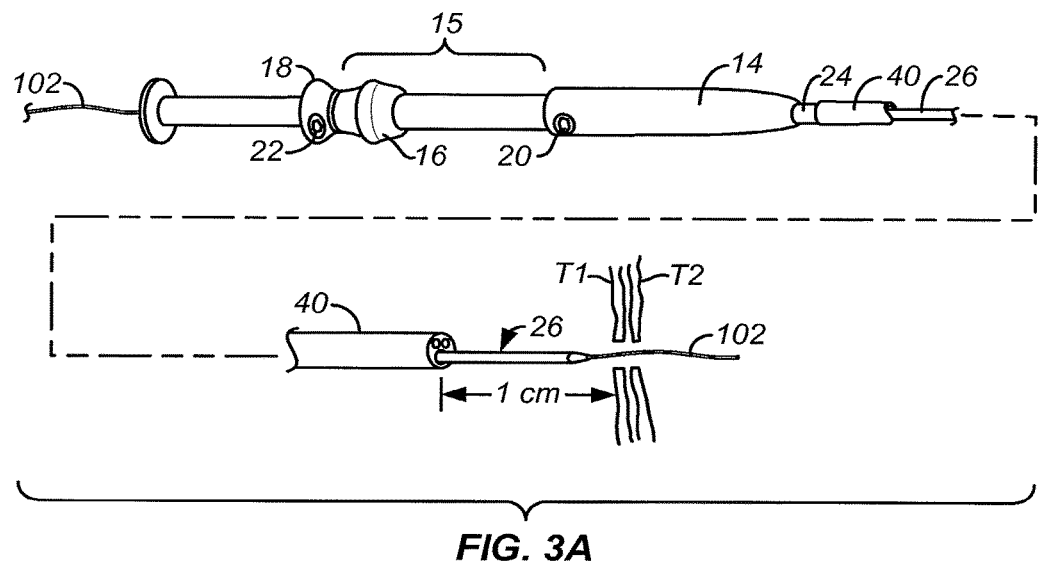
FIGS. 3A-3E illustrate use of the stent deployment apparatus of FIG. 1 for deploying a stent through apposed luminal walls according to the principles of the methods of the present invention.

The catheter body 26 is then advanced over the guidewire 102 through the working channel of the endoscope 40 and is secured to the proximal end of a working channel using scope locking mechanism 24 to locate the catheter body 26 with a tip 32 approximately 1 cm outside of the distal end of the working channel, as in FIG. 3A.

Figure 3B:
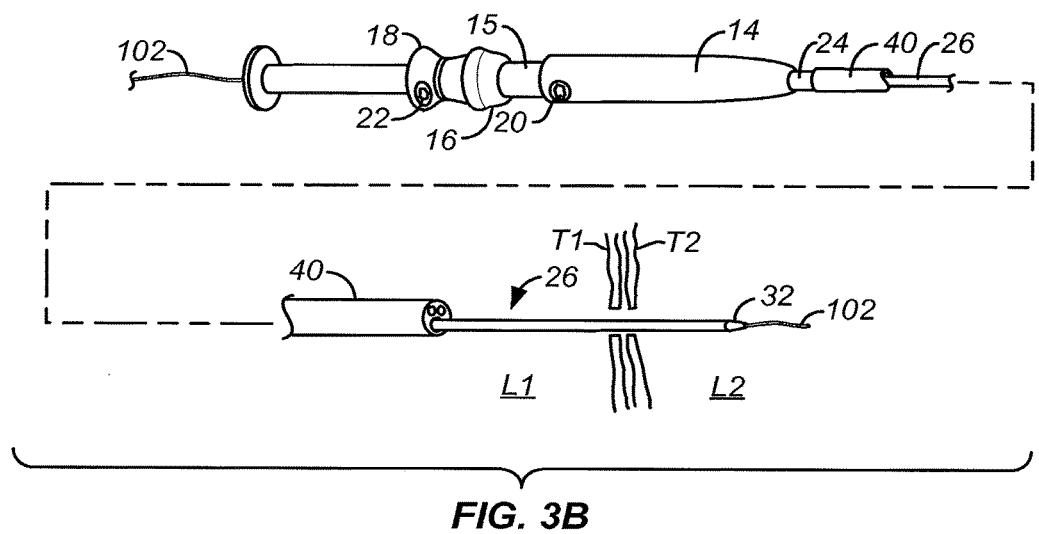
Figure 3C:
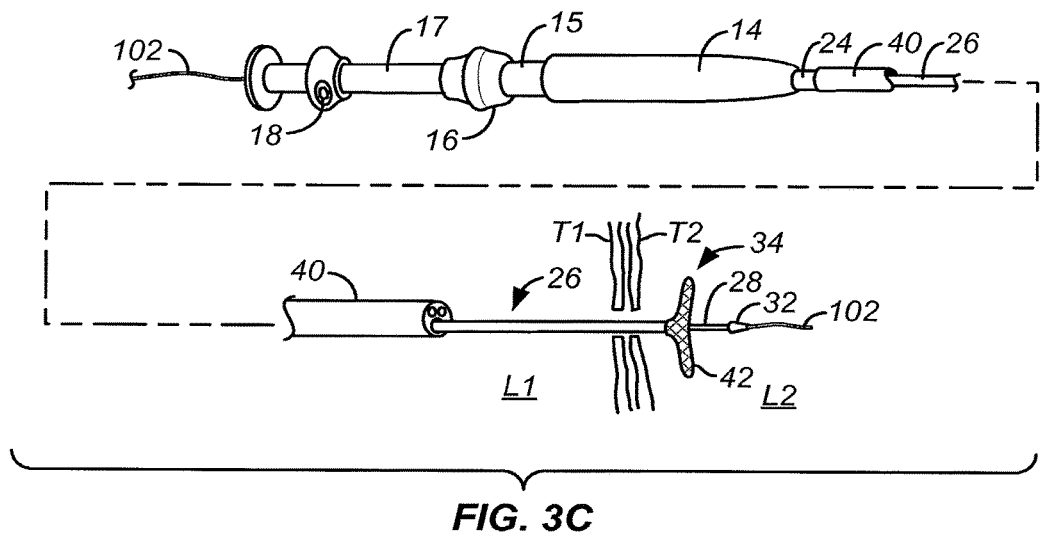

The first slide actuator 15 is distally advanced using knob 16, after releasing lock 20, on handle 12, thus moving the assembly of catheter body 26, shaft 28, and stent 34, in the distal direction and through the tract formed through tissue T1 and tissue T2 and moving distal tapered tip 32 from lumen L1 to lumen L2 as in FIG. 3B. Lock 20 is then reengaged, securing first slide actuator 15 to control handle body 14.

A distal flange segment 42 of the tissue anchor 34 is now expanded by moving the second slide actuator 18 in the proximal direction to retract sheath 27. The second slide actuator is pulled back to a predetermined position part way along the proximal extension 17 of the first slide actuator 15, after releasing second lock 22 as in FIG. 3C. A portion of lock 22 (FIG. 1) of second slide actuator 18 moves in a track (not shown), where said lock 22 engages a stop at a predetermined position, thereby stopping the proximal movement of actuator 18. Said predetermined position is calibrated to allow only the distal flange 42 of tissue anchor 34 to be released from constraint by sheath 27 and to expand. Said proximal motion of second slide actuator 18 retracts the sheath 27, while the shaft 28 is held in place, this releasing the distal portion of tissue anchor 34 from constraint.

Figure 3D:
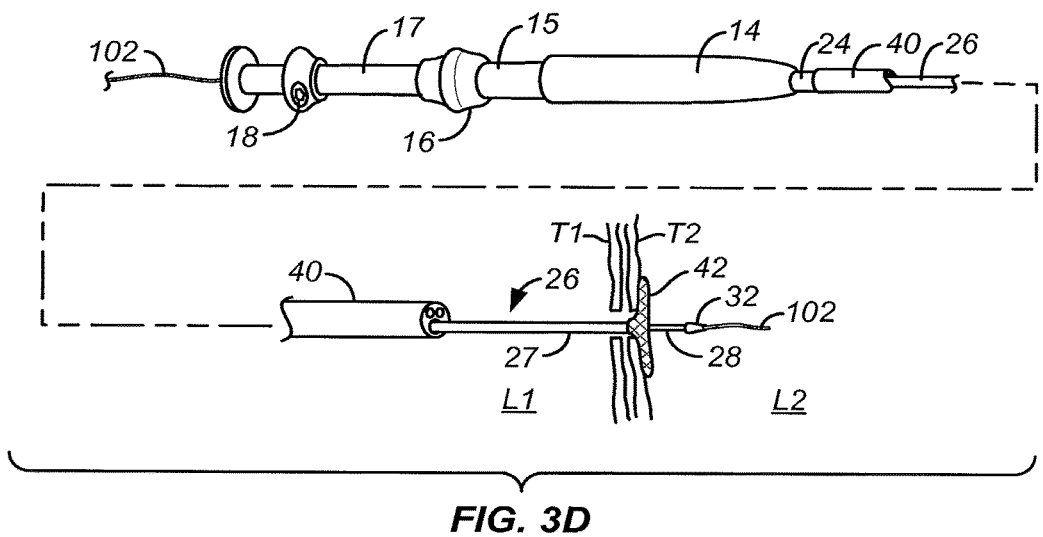

The first slide actuator 15 is now moved slowly in the proximal direction using knob 16, after releasing lock 20, on handle 12, thus moving the expanded distal anchor flange 42 against the inner surface of tissue T2 of lumen L2, and positioning tissue T1 closer to tissue T2, holding lumen L1 and L2 in close apposition as in FIG. 3D. Stent lock 30 (FIG. 2) holds the proximal end of the tissue/stent anchor 34 firmly allowing proximal traction against tissue T2. Lock 20 is then reengaged, securing first slide actuator 15 to control handle body 14.

Figure 3E:
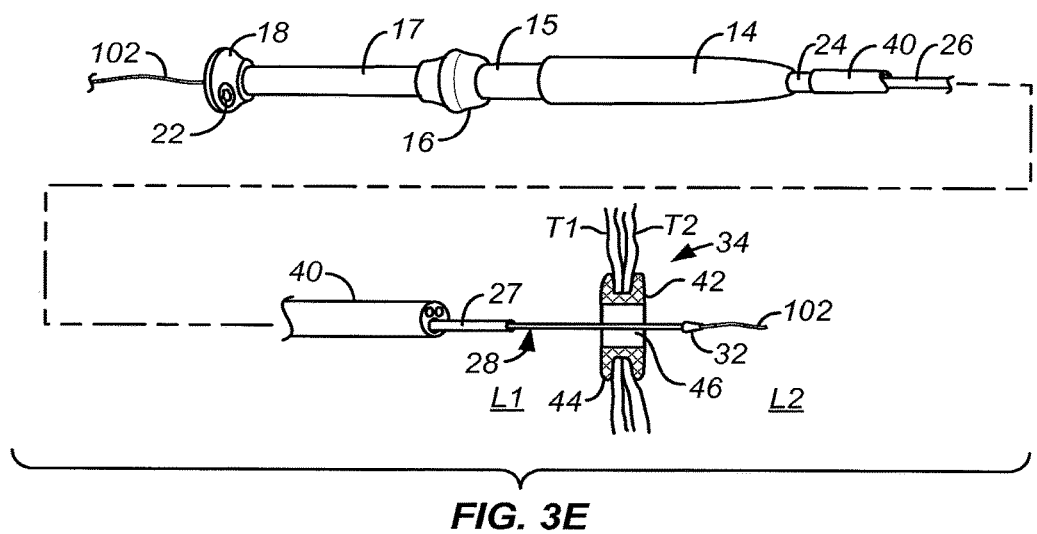

A proximal segment 44 of the tissue anchor stent 34 is now expanded by moving the second slide actuator 18 in the proximal direction to a position at or near the proximal end of the first slide actuator 15, after releasing lock 22 as in FIG. 3E to further retract the sheath 27. The proximal end of the tissue anchor stent 34 releases from stent lock 30 (FIG. 2) as the second slide actuator 18 reaches the proximal end of its travel. This releases the entire tissue anchor, which in this example has a central lumen 46 allowing fluid communication between lumens L1 and L2. The device 10 is now removed, leaving the tissue anchor 34 with central lumen 46 implanted between lumen L1 and lumen L2 with fluid communication being established.

Of particular interest in advanced therapeutic endoscopy is the drainage of bile from the gallbladder into the duodenum or stomach. This is accomplished endoscopically from within the GI lumen of the duodenum or stomach and requires that the gallbladder be located using transluminal imaging, such as endoscopic ultrasound (EUS), followed by penetration through the GI lumen and gallbladder wall and precise placement of a drainage stent between these structures. During the placement of the drainage stent, it is necessary that close apposition of the gallbladder and GI lumen be maintained to prevent bile leakage into the peritoneal cavity, a situation that can cause peritonitis which can be fatal. In this instance, delivery of a tissue anchor or luminal approximating stent requires precise control allowing that close apposition is maintained throughout the procedure and throughout the course of therapy. Using the devices of the present invention tissue stents and anchors, such as those described above or in co-pending application US 2009/0281557, can be precisely delivered.

An alternative embodiment of the stent deployment system of the present invention is illustrated in FIGS. 4 and 5A-5E. This alternative system is specifically designed for direct delivery and implantation of the stent or other anchor without use of a guidewire and allows the manipulation of all components of the system to form a single handle while the handle is secured to an endoscope used to access the first body lumen to provide a stable implant delivery platform. The components of the system have been optimized to minimize the risk of body fluid leakage during the stent or anchor implantation procedure, particularly enhancing the seal maintained on the penetration through the wall of the second body lumen to reduce leakage from that lumen.

Figure 4:
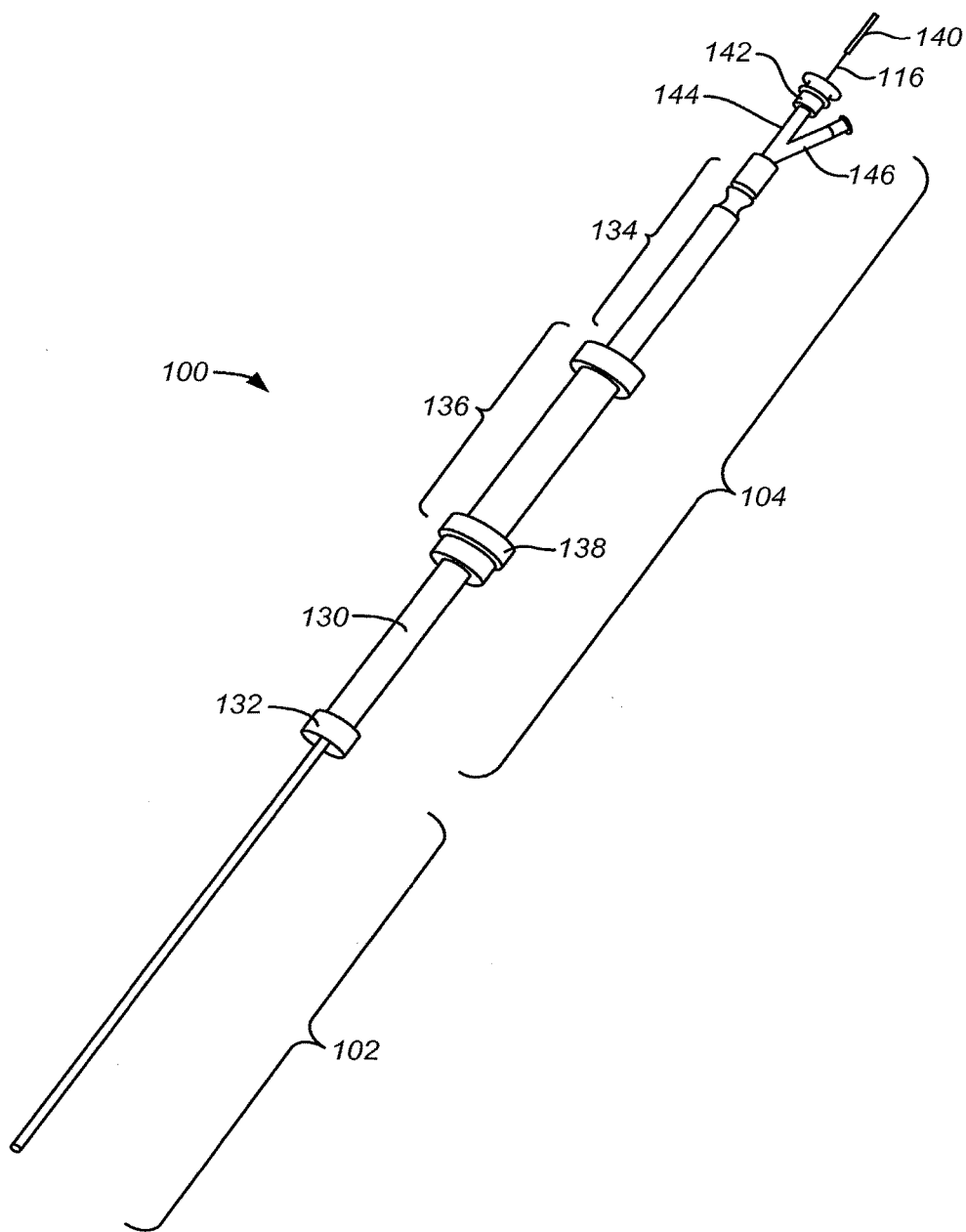
FIG. 4 illustrates a second embodiment of the stent deployment apparatus of the present invention.
Figure 5A:
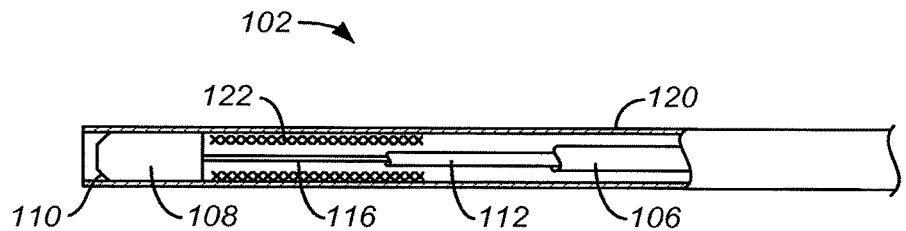
FIGS. 5A-5E illustrate sequential actuation of the various tools of the stent deployment apparatus of FIG. 4.
Figure 5B:
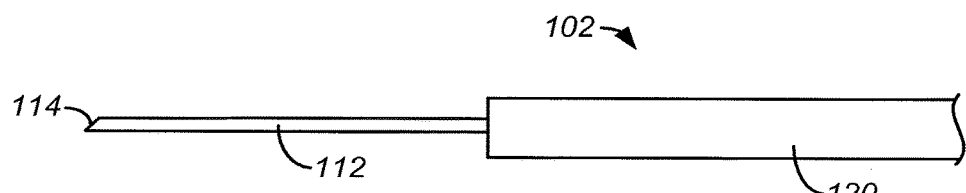
Figure 5C:
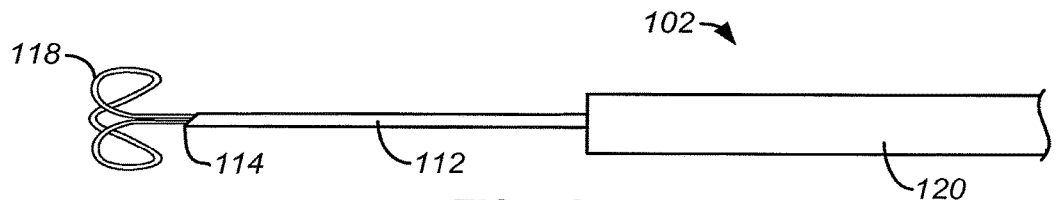
Figure 5D:
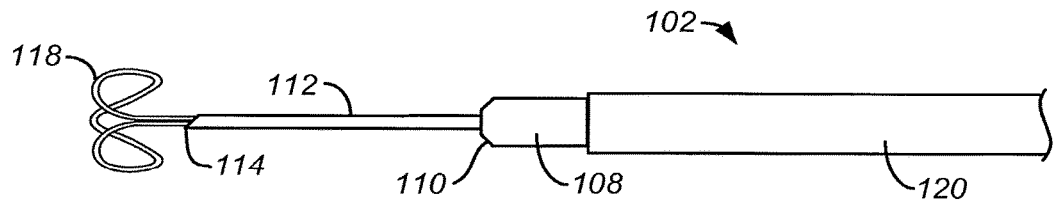
Figure 5E:
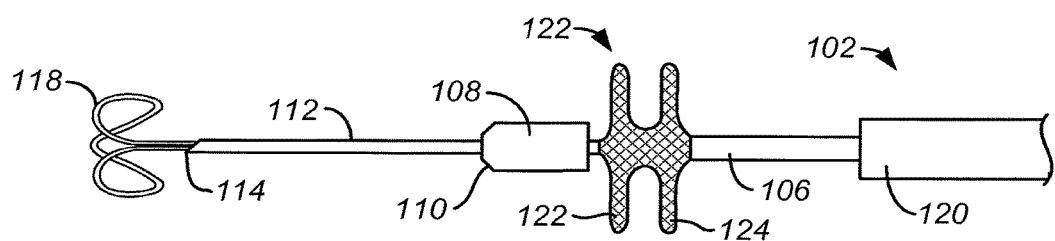

As shown in FIG. 4, the alternative stent delivery system 100 comprises a catheter 102 attached at its proximal end to a distal end of a handle assembly 104. The catheter 102 includes a plurality of coaxially disposed components as best seen in FIGS. 5A-5E. A catheter shaft 106 extends the entire length of the catheter (a portion of the distal end is broken away to show internal components) and is attached at its distal end to a tapered tip 108 which includes a leading end 110 usually has includes a cutting edge or element to cut tissue as the tip is advanced therethrough. A needle 112 having a tissue-penetrating tip 114 is slidably received within an axial passage of the shaft 106 so that the needle can be extended distally beyond the distal end of the catheter, as shown in FIG. 5B, even when all other components are maintained within the catheter. A tension wire 116 is slidably disposed within an axial passage of the needle 112 and includes an anchor structure 118 which can be deployed when it is extended distally beyond the tip 114 of the needle 112, as illustrated in FIG. 5C. The entire catheter 102 (distal to the handle 104) is covered by a retractable sheath 120, and the sheath maintains radial constraint on a self-expanding stent 122 or other anchor, allowing deployment of the stent by refraction of the sheath, as shown in FIG. 5E. The catheter 102 is shown in its initial delivery configuration in FIG. 5A where all system components are retracted within the sheath, with the needle 112 retracted within the shaft 106, and the tension wire 116 retracted within the needle. In FIG. 5A, the needle 112 is shown distally extended beyond the distal end of the remaining components in the catheter 102. In FIG. 5C, the anchor structure 118 of the tension wire 116 is shown distally extended beyond the distal tip 114 of the needle. In FIG. 5D, the sheath 120 is shown retracted relative to the shaft so that at least the cutting edge 110 of the tapered tip 108 is exposed beyond the distal end of the sheath 120. Finally, in FIG. 5E, the catheter 102 is shown with all components fully extended (except for the sheath 120 which is retracted) and with the stent 122 shown in its radially expanded configuration having a proximal flange 124 and a distal flange 122.

Figure 6A:
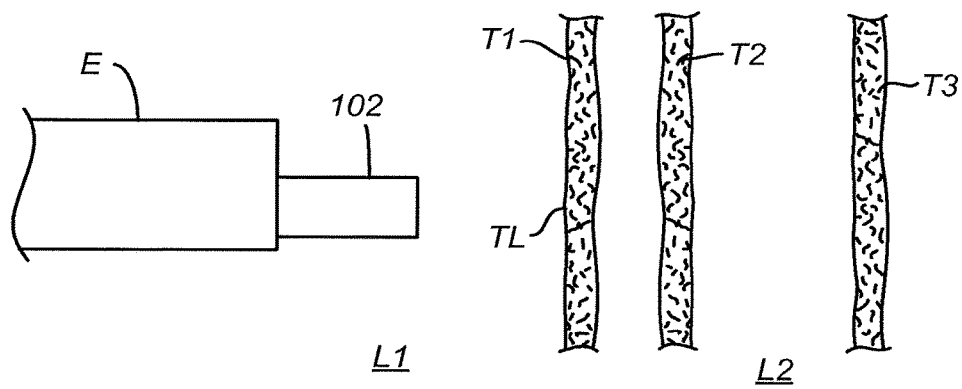
FIGS. 6A-6G illustrate use of the apparatus of FIG. 4 for deploying a stent across apposed luminal walls in accordance with the principles of the methods of the present invention.

The handle assembly 104 comprises a plurality of slide actuators which permit selective advancement and retraction of the various components of the catheter 102, as will now be described. The handle assembly 104 includes a body 130 having a coupling member 132 at its distal end. The coupling member 132 is selectively attachable to the proximal hub of an endoscope E (as shown in FIG. 6A) after the catheter 102 has been introduced through the working channel. From that point on in any procedure, the body 130 of the handle assembly 104 will remain fixed relative to the endoscope while the remaining components in the handle may be selectively advanced and retracted in order to deploy the various components of the catheter. In particular, a first tubular slider 134 is coupled to advance the needle and tension wire when it is pushed forward relative to the body 130. A second tubular slider 136 is coupled to the catheter shaft and sheath in order to advance the shaft and sheath in unison when the slider 136 is pushed forward relative to the body 130. The first and second tubular sliders 134 and 136, however, are decoupled so that manipulation of the first tubular slider does not affect the position of the shaft and sheath while manipulation of the second tubular slider 136 does not affect the position of the needle and tension wire.

The sheath may be retracted relative to the shaft and other system components using a collar 138 which is slidably disposed over the second tubular slider 136. Refraction of the collar 138 retracts the sheath but leaves all other system components stationary relative to the body 130 and endoscope to which it is attached. A proximal handle 140 at the proximal end of the tension wire 116 extends out from a Touhy Borst fitting 142 when a Y-connector 144 attached to the proximal end of the needle 112. The Y-connector 144 also includes an aspiration/infusion port 146 which is fluidly coupled to the central passage of the needle. The tension wire 140 may be advanced and retracted relative to all other system components by loosening the Touhy Borst fitting and manually advancing or retracting the handle 140.

By manually advancing the tension wire 116 using the handle 140, the anchor structure 118 is deployed. Usually, the anchor structure 118 is pre-shaped to assume a desired configuration when it is released from the confinement of the needle lumen. Conveniently, the anchor structure and the entire tension wire may be formed from Nitinol or other shape-memory alloy. In the exemplary elements, the anchor structure 118 comprises a plurality of loops which deploy rearwardly to form a concave structure (with the concave surface in the rearward or proximal direction), as illustrated in FIGS. 5C-5E. The structure may be foamed from a single length of the wire which folds back on itself to form the illustrated structure. Alternatively, the wire could be split to form the multi-loop structure from a single larger loop. A variety of other geometries and structures could be provided for the anchor structure, including cones, conical spirals, multiple everting elements, and the like.

A detailed construction for the catheter handle showing the connections between the handle components and the catheter components is provided in Appendix A attached to this application.

Referring now to FIGS. 6A-6G, the stent deployment system 100 is illustrated in use for implanting stent 122 between tissue layers T1 and T2 and body lumens L1 and L2. Body lumen L2 has a back wall T3 which is to be protected during the procedure. As shown in FIG. 6A, an endoscope E is positioned within the body lumen L1, and the distal end of the catheter 102 is advanced through a working channel of the endoscope to be positioned adjacent to a target location TL on the luminal wall T1 of body lumen L1. Usually, visualization using the endoscope will be sufficient to properly locate the target location, but use of fluoroscopy, endoscopic ultrasound, or other imaging modes would also be possible.

Figure 6B:
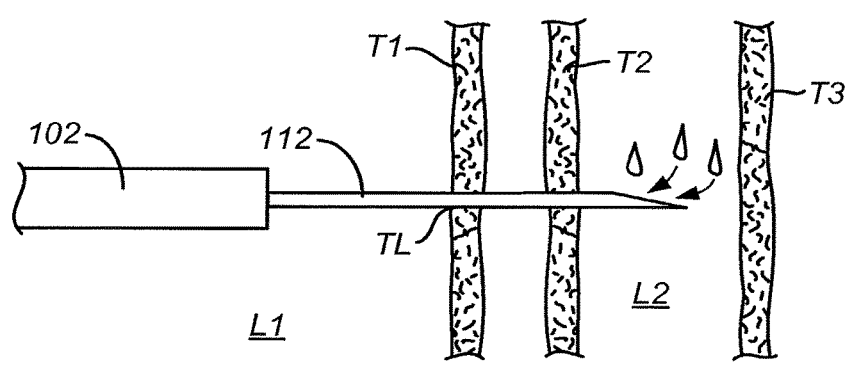

After the target location TL has been identified, the needle 112 will be advanced through the target location on T1 and through a corresponding location on T2, as shown in FIG. 6B. The endoscope is not shown in FIGS. 6B-6G, but it would still be present as the catheter handle assembly 104 would have been connected to a proximal hub on the endoscope prior to needle advancement. The needle will be advanced by distally advancing the first tubular slider 134. Successful entry into the lumen L2 can be confirmed by aspirating fluid through the needle lumen and port 146 on the Y-connector 144. Usually, a lock or a limiter (not shown) will be provided on the handle assembly 104 so that forward advancement of the first tubular slider 134 is stopped at a depth which prevents penetration through the back wall T3 of the lumen L2.

Figure 6C:
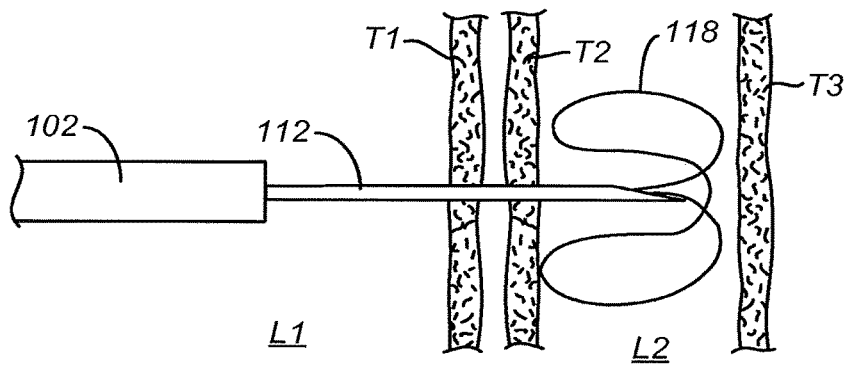

Once the needle 112 has successfully reached the interior of body lumen L2, the anchor structure 118 will be deployed, as shown in FIG. 6C. Deployment is conveniently achieved by advancing handle 140 at the proximal end of the tension wire 116 to deploy the multi-lobed structure as described previously.

Once the anchor structure 118 has been successfully deployed, the needle 112 and tension wire 116 may be retracted relative to the remaining components of the catheter and the endoscope in order to draw the anchor 118 proximally to close the tissue walls T1 and T2 closer together, as also shown in FIG. 6C.

Figure 6D:
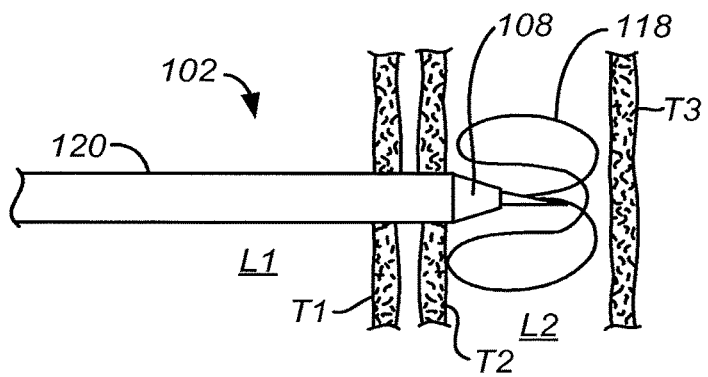

After the tissue walls T1 and T2 are drawn into closer apposition, the tapered tip 114 of the catheter 102 may be exposed by partially retracting the sheath 120, as shown in FIG. 6D, and the catheter advanced through the needle penetration with the tapered tip (usually including a cutting element) facilitating advancement and enlarging the penetration. Continued tension on the needle 112 and tension wire 116 help maintain apposition between tissue layers T1 and T2 during advancement of the catheter to reduce the risk of body fluid leakage from either body lumen, particularly from the target lumen L2.

Figure 6E:
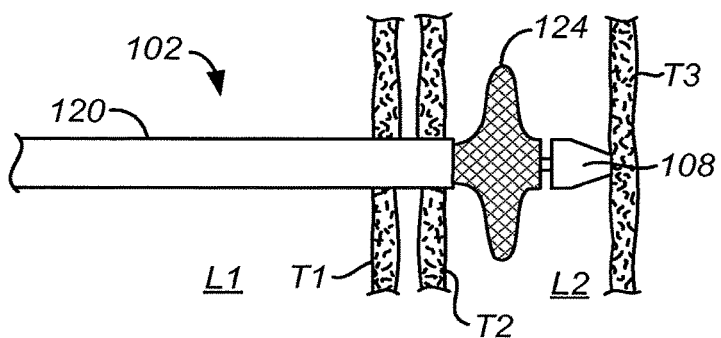
Figure 6F:
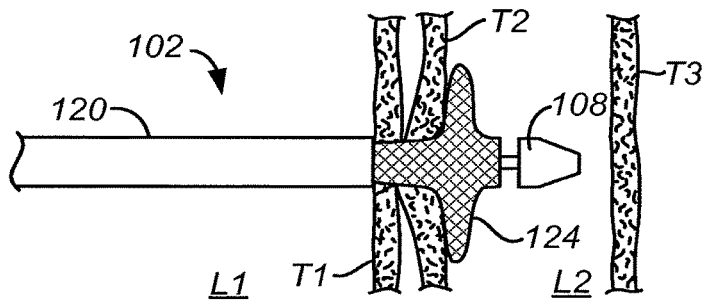
Figure 6G:
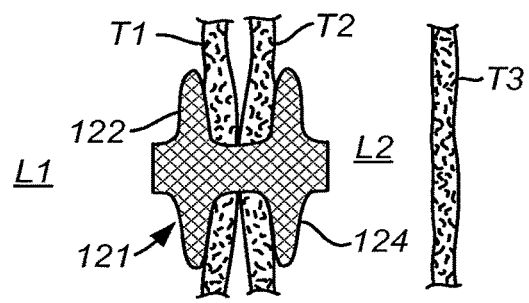

Once the catheter 102 has successfully entered second body lumen L2, as shown in FIG. 6E, the proximal flange 124 of the stent 122 may be deployed by further retracting the sheath 120 and the needle 112 and anchor structure 118 can be withdrawn. The proximal flange may then be drawn proximally against the wall of T2, as shown in FIG. 6F to reestablish apposition of the luminal walls during the remainder of the deployment procedure. The flange 124 may be retracted using the second tubular slider 136 which is coupled to the shaft which carries the stent. A stent lock (not shown) or other structure is provided to prevent the stent from sliding over the shaft during the deployment procedure prior to full expansion of the stent. After the tension has been applied using the distal flange 124, the sheath 120 may be further retracted, using sheath collar 138, to fully deploy the stent so that the proximal flange 122 engages a luminal surface of the first tissue layer T1, as shown in FIG. 6G. After the stent is deployed, the catheter including all components may be removed by detaching the handle from the endoscope and withdrawing the entire structure. A central passage or opening through the stent provides for a fluid communication between lumens L1 and L2, typically for drainage of fluids from second body lumen L2 into the first body lumen L1.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a stent from a first body lumen to a second body lumen through apposed walls of said lumens, said method comprising:
    positioning an endoscope in the first body lumen adjacent to a target site on the wall of the first body lumen, which is a luminal wall;
    advancing a catheter assembly in a working channel of the endoscope to locate a distal region of the catheter assembly at the target site;
    advancing a portion of the catheter assembly through a hole in the apposed walls at the target site, the catheter assembly including a stent deployment sub-assembly;
    expanding a distal flange on the stent in the second body lumen by retracting a sheath;
    stopping the retraction of the sheath at a pre-determined distance that is less than a length of the stent;
    drawing proximally on the stent deployment sub-assembly to pull the distal flange against the wall of the second body lumen to maintain the walls in apposition; and
    after drawing proximally, expanding a proximal flange on the stent in the first body lumen to complete delivery by further retracting the sheath.

2. The method as in claim 1, wherein the stent is self-expanding and the sheath is part of the stent deployment sub-assembly.

3. The method as in claim 1, wherein the first body lumen is selected from the group consisting of an esophagus, a stomach, a duodenum, a small intestine, a large intestine, and the second body lumen is selected from the group consisting of a bile duct, a pancreatic duct, a gallbladder, a cyst, a pseudocyst, an abscess, a pancreas, a liver, an urinary bladder, a duodenum, a jejunum, and a colon.

4. The method as in claim 1, wherein a needle is carried by the catheter assembly.

5. The method as in claim 1, wherein during advancing the portion of the catheter assembly the stent deployment sub-assembly carries the stent over a needle.

6. The method as in claim 1, further comprising penetrating the apposed walls at the target site to form the hole in the apposed walls.

7. The method as in claim 1, further comprising:
    deploying an anchor on a distal end of a tension wire in the second body lumen;
    drawing proximally on the tension wire to maintain the walls in close apposition;
    advancing the stent deployment sub-assembly while maintaining tension on the tension wire.

8. The method as in claim 7, wherein deploying the anchor comprises advancing the tension wire through an axial passage of a needle after the needle has penetrated through the apposed walls.

9. The method as in claim 8, wherein the anchor is a self-expanding structure formed integrally with the tension wire.

10. The method as in claim 9, wherein the self expanding anchor structure deploys as the tension wire is advanced from the needle causing the anchor to be released from the axial passage of the needle and to cover a distal tip of the needle.

11. The method as in claim 1, further comprising forming the hole in the apposed walls at the target site using a needle prior to advancing the portion of the catheter assembly through the hole in the apposed walls at the target site.

12. The method of claim 11, wherein the needle is an electrosurgical needle.

13. The method as in claim 1, wherein expanding the distal flange on the stent in the second body lumen forms a double-walled flange.

14. The method as in claim 1, wherein expanding the distal flange on the stent in the second body lumen forms a lip on a distal side of the distal flange, wherein the lip on the distal side of the distal flange has an expanded diameter that is less than an expanded diameter of the distal flange on the stent.

15. The method as in claim 1, wherein expanding the proximal flange on the stent in the first body lumen forms a double-walled flange.

16. The method as in claim 1, wherein expanding the proximal flange on the stent in the first body lumen forms a lip on a proximal side of the proximal flange, wherein the lip on the proximal side of the proximal flange has an expanded diameter that is less than an expanded diameter of the proximal flange on the stent.

17. The method as in claim 1, wherein the second body lumen comprises a gallbladder.

18. The method as in claim 1, wherein the first body lumen is a stomach or duodenum.

19. The method as in claim 1, wherein the first body lumen is a stomach and the second body lumen is a pseudocyst, jejunum, or duodenum.

20. The method as in claim 1, wherein the second body lumen is a colon.

21. The method as in claim 1, wherein retracting the sheath to the pre-determined distance includes retracting the sheath to a locking point on the catheter assembly.

22. The method as in claim 21, further comprising unlocking the sheath prior to expanding the proximal flange.

23. The method as in claim 1, wherein the pre-determined distance is calibrated to allow only the distal flange of the stent to be released.

24. The method as in claim 1, wherein expanding the proximal flange on the stent in the first body lumen forms a fluid communication pathway through the stent between the first body lumen and the second body lumen.

* * * * *